United States Patent [19]

Ueda et al.

[11] Patent Number: 4,564,621
[45] Date of Patent: Jan. 14, 1986

[54] α-ARYL-α-PYRIDYLALKANOIC ACID DERIVATIVES, PROCESS FOR PREPARATION THEREOF AND PHARMACEUTICAL COMPOSITION COMPRISING THE SAME

[75] Inventors: Ikuo Ueda, Toyonaka; Masanobu Nagano, Suita; Atsushi Akahane, Ikeda, all of Japan

[73] Assignee: Fujisawa Pharmaceutical Co., Ltd., Osaka, Japan

[21] Appl. No.: 535,298

[22] Filed: Sep. 23, 1983

[30] Foreign Application Priority Data

Sep. 30, 1982 [JP] Japan .............................. 57-172936

[51] Int. Cl.$^4$ .................... C07D 213/38; A61K 31/44
[52] U.S. Cl. ................................... 514/357; 546/193; 546/276; 546/281; 546/330; 546/333; 544/124; 544/360; 514/227; 514/252; 514/318; 514/341; 514/343
[58] Field of Search ................ 546/330, 333; 514/357

[56] References Cited

U.S. PATENT DOCUMENTS 2,991,289 7/1961 Schulte .............................. 546/333

FOREIGN PATENT DOCUMENTS

| 501690 | 7/1954 | Canada | 546/333 |
| 29578 | 7/1973 | Japan | 544/360 |
| 666778 | 2/1952 | United Kingdom | 546/333 |
| 771814 | 4/1957 | United Kingdom | 546/333 |

Primary Examiner—Marion C. McCamish
Assistant Examiner—S. A. Gibson
Attorney, Agent, or Firm—Oblon, Fisher, Spivak, McClelland & Maier

[57] ABSTRACT

New α-aryl-α-pyridylalkanoic acid derivatives of the formula:

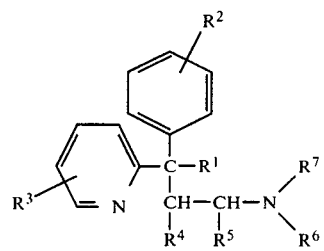

wherein $R^1$ is cyano or carbamoyl,
$R^2$ is hydrogen or halogen,
$R^3$ is hydrogen or lower alkyl,
one of $R^4$ and $R^5$ is hydrogen and another is lower alkyl,
$R^6$ is hydrogen or lower alkyl, and
$R^7$ is lower alkyl, or
$R^6$ and $R^7$ are taken together to form an N-containing saturated heterocyclic group with the adjacent nitrogen atom, in which the heterocyclic group may be substituted with lower alkyl or optionally protected hydroxy(lower)alkyl, provided that $R^2$ is halogen or $R^3$ is lower alkyl, when $R^1$ is cyano and $R^6$ and $R^7$ are each lower alkyl, and salts thereof, and processes for preparation thereof and pharmaceutical composition comprising the same.

These derivatives and salts thereof are useful as anti-ulcer agents and spasmolytic agents.

5 Claims, No Drawings

α-ARYL-α-PYRIDYLALKANOIC ACID DERIVATIVES, PROCESS FOR PREPARATION THEREOF AND PHARMACEUTICAL COMPOSITION COMPRISING THE SAME

The present invention relates to novel α-aryl-α-pyridylalkanoic acid derivatives and pharmaceutically acceptable salts thereof. More particularly, it relates to novel α-aryl-α-pyridylalkanoic acid derivatives and pharmaceutically acceptable salts thereof which have inhibitory activity on ulcer and spasm, to process for preparation thereof, to pharmaceutical composition comprising the same, and to method of using the same therapeutically in the treatment of ulcer and spasm in human being and animals.

Accordingly, one object of this invention is to provide novel α-aryl-α-pyridylalkanoic acid derivatives and pharmaceutically acceptable salt thereof, which are useful as a medicine for ulcer and spasm.

Another object of this invention is to provide process for preparation of said α-aryl-α-pyridylalkanoic acid derivatives and pharmaceutically acceptable salts thereof.

A further object of this invention is to provide pharmaceutical composition comprising, as an active ingredient, said α-aryl-α-pyridylalkanoic acid derivative or its pharmaceutically acceptable salt.

Still further object of this invention is to provide method of using said α-aryl-α-pyridylalkanoic acid derivative or its pharmaceutically acceptable salt in the treatment of ulcer and spasm in human being and animals.

Some α-aryl-α-pyridylalkanoic acid derivatives having similar chemical structure have been known. For example, α-phenyl-α-(2-pyridyl)-4-(N,N-diisopropylamino)butyramide (U.S. Pat. No. 3,225,054) and α-phenyl-α-(2-pyridyl)-4-(N,N-dimethylamino)-3-methylbutyronitrile (British Pat. No. 666,778) have been known. The former compound is actually used as an antiarrhythmic agent and the latter compound possesses antihistaminic activity, but it has not been known that these compounds possess inhibitory activity on ulcer or spasm.

The α-aryl-α-pyridylalkanoic acid derivatives of this invention are novel and can be represented by the following general formula [I]:

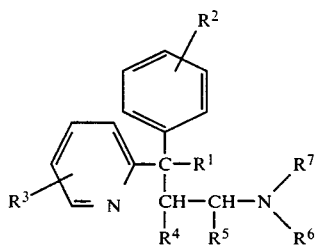

wherein
$R^1$ is cyano or carbamoyl,
$R^2$ is hydrogen or halogen,
$R^3$ is hydrogen or lower alkyl,
one of $R^4$ and $R^5$ is hydrogen and another is lower alkyl,
$R^6$ is hydrogen or lower alkyl, and
$R^7$ is lower alkyl, or
$R^6$ and $R^7$ are taken together to form an N-containing saturated heterocyclic group with the adjacent nitrogen atom, in which the heterocyclic group may be substituted with lower alkyl or optionally protected hydroxy(lower)alkyl, provided that $R^2$ is halogen or $R^3$ is lower alkyl, when $R^1$ is cyano and $R^6$ and $R^7$ are each lower alkyl.

In the above formula [I], suitable halogen for $R^2$ may be chlorine, bromine, iodine or fluorine.

Suitable lower alkyl for $R^3$, $R^4$, $R^5$, $R^6$ and $R^7$ may be methyl, ethyl, propyl, isopropyl, butyl, isobutyl, tert-butyl, pentyl, hexyl or the like.

The N-containing saturated heterocyclic group which is formed by $R^6$, $R^7$ and the adjacent nitrogen atom may be 1-piperazinyl, piperidino, morpholino, 1-pyrrolidinyl, 1-pyrazolidinyl or the like. These N-containing saturated heterocyclic group may be substituted with lower alkyl or hydroxy(lower)alkyl which may optionally be protected. Suitable examples of said lower alkyl group and lower alkyl moiety of the optionally protected hydroxy(lower)alkyl group may be the same as those exemplified before. Suitable examples of the optionally protected hydroxy moiety may be hydroxy or hydroxy protected by a conventional hydroxy protective group such as acyl [e.g. formyl, acetyl, lauroyl, ethoxycarbonyl, tert-butoxycarbonyl, methanesulfonyl, benzoyl, etc.], ar(lower)alkyl [e.g. benzyl, 4-nitrobenzyl, etc.] or the like.

Suitable salt of the object compounds [I] may be an inorganic acid addition salt [e.g. hydrochloride, hydrobromide, sulfate, etc.], or an organic acid addition salt [e.g. acetate, tartrate, citrate, methanesulfonate, etc.].

The object compounds [I] and salts thereof can be prepared by following methods.

Process 1

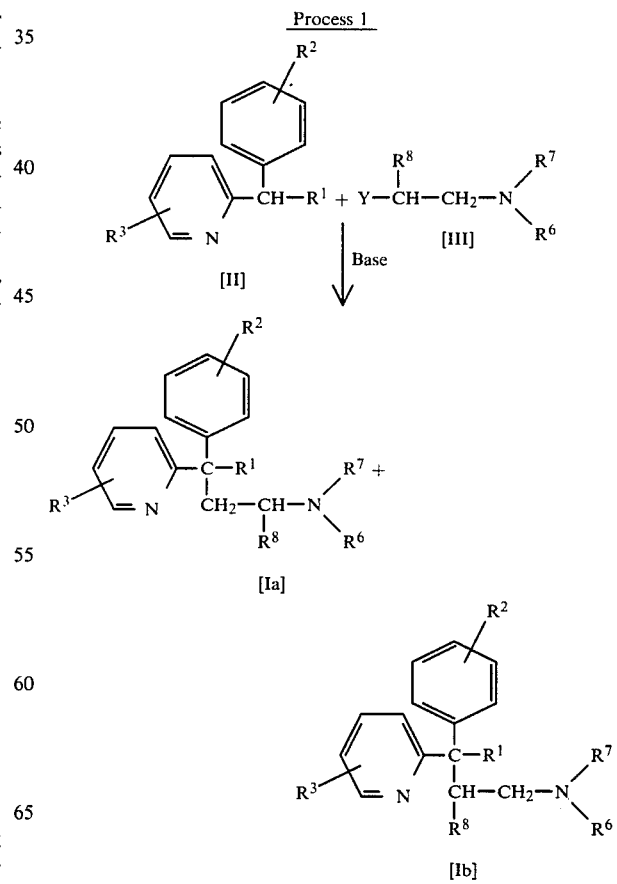

-continued
Process 2

[Structure Ic: Aromatic ring with R² substituent, connected to another ring with R³ and N, bearing C—CN group, CH—CH—N with R⁴, R⁵, R⁶, R⁷ substituents] → Hydrolysis →

[Structure Id: Aromatic ring with R² substituent, connected to another ring with R³ and N, bearing C—CONH₂ group, CH—CH—N with R⁴, R⁵, R⁶, R⁷ substituents]

wherein
$R^8$ is lower alkyl,
Y is a leaving group, and
$R^1$, $R^2$, $R^3$, $R^4$, $R^5$, $R^6$ and $R^7$ are each as defined before, provided that $R^2$ is halogen or $R^3$ is lower alkyl, when $R^1$ is cyano and $R^6$ and $R^7$ are each lower alkyl.

In the above reaction schemes, suitable examples of the lower alkyl group for $R^8$ may be the same as those exemplified for the compounds [I]. Suitable examples of the leaving group for Y may be halogen mentioned before, tosyloxy, mesyloxy or the like.

The processes for preparing the object compounds [I] are explained in detail in the following.

PROCESS 1

The object compounds [Ia] and [Ib] and salts thereof can be prepared by reacting a compound [II] or its salt with a compound [III] or its salt in the presence of a base.

Suitable salts of the compounds [II] and [III] may be the same as those exemplified for the object compounds [I].

The base to be used in this reaction may be metal alkoxide [e.g. sodium methoxide, sodium ethoxide, potassium tert-butoxide, etc.], metal amide [e.g. sodium amide, lithium diisopropylamide, etc.], metal hydride [e.g. sodium hydride, calcium hydride, etc.], organic metal compound [e.g. n-butyl lithium, methyl lithium, phenylsodium, etc.], alkali metal hydroxide [e.g. sodium hydroxide, potassium hydroxide, etc.] or the like.

This reaction is usually carried out in a conventional solvent such as alcohol [e.g. methanol, ethanol, tert-butyl alcohol, etc.], aromatic hydrocarbon [e.g. benzene, xylene, etc.], aliphatic hydrocarbon [e.g. hexane, heptane, etc.], ether [e.g. diethyl ether, tetrahydrofuran, etc.], dimethylformamide, water or the like. These solvents may be selected according to the kind of starting compound and base to be used.

The reaction temperature is not critical, and the reaction is usually carried out at temperature range from room temperature to heating.

The reaction is occasionally carried out preferably under an inert atmosphere such as in a stream of nitrogen gas depending upon the kind of the base to be used.

The reaction product contains both of the object compounds [Ia] and [Ib], because the reaction using the starting compound [III] seems to proceed through the ethyleneimmonium ion as an intermediate. Each of the object compounds [Ia] and [Ib] include isomers due to asymmetric carbon atoms in the molecule. These isomers can be isolated and purified by a conventional manner such as column chromatography, recrystallization, distillation, optical resolution or the like.

PROCESS 2

The object compound [Id] and its salt can be prepared by hydrolyzing a compound [Ic] or its salt.

This reaction is usually carried out in the presence of an acid or a base.

Suitable examples of the acid may be sulfuric acid, hydrochloric acid, hydrobromic acid, phosphoric acid or the like. Suitable examples of the base may be sodium hydroxide, potassium hydroxide, sodium carbonate, sodium bicarbonate, triethylamine, pyridine, 1,8-diazabicyclo(5.4.0)-7-undecene or the like.

This reaction is usually carried out in water or hydrous solvent such as hydrous methanol, hydrous ethanol, hydrous dioxane, hydrous tetrahydrofuran, hydrous dimethylformamide or the like. In case that the acid or base to be used is liquid, it can also be used as a solvent.

The reaction temperature is not critical, and the reaction is usually carried out at temperature range from ambient temperature to heating.

The object compounds [Id] include isomers due to asymmetric carbon atoms in the molecule. These isomers can be isolated and purified by a conventional manner such as column chromatography, optical resolution or the like.

The object compounds [I] obtained by above Process 1 and 2 can be optionally converted into salts as mentioned before.

It is to be noted that each of the object compounds [I] and the starting compounds [II] and [III] include one or more steroisomers due to asymmetric carbon atoms in the molecule, and all of such isomers of the compounds [I], [II] and [III] are included within the scope of this invention.

The object compounds [I] and their pharmaceutically acceptable salts of the present invention possess an anti-ulcer activity and spasmolytic activity, and are useful for a therapeutic treatment of ulcer and spasm.

For therapeutic purpose, the compounds according to the present invention can be used in a form of pharmaceutical preparation containing said compound as an active ingredient, in admixture with a pharmaceutically acceptable carrier such as an organic or inorganic solid or liquid excipient suitable for oral or parenteral administration. The pharmaceutical preparations may be capsules, tablets, dragees, solution, suspension, emulsion, and the like. If desired, there may be included in the above preparations auxiliary substances, stabilizing agents, wetting or emulsifying agents, buffers and other commonly used additives.

While the dosage of the compounds will vary depend upon the age and condition of the patient, an average single dose of about 5 mg, 10 mg, 50 mg, 100 mg, 250 mg, 500 mg, and 1000 mg of the compounds according to the present invention may be effective for treating ulcer and spasm. In general, amounts between 1 mg/body and about 1000 mg/body or even more may be administered per day.

In order to illustrate the usefulness of the object compound [I], antiulcer activity [i.e. gastric secretion in Heidenhain pouch dogs, inhibition on stress ulcer and inhibition on ethanol ulcer] and spasmolytic activity are shown in the following.

(I) ANTIULCER ACTIVITY

Test Method (i) Test A

Gastric secretion in Heidenhain pouch dogs

Beagle dogs, weighing about 8–13 kg, were used for the study on gastric secretion. The animals were surgically provided with a vagally denervated Heidenhain pouch. One month or more later, the dogs were fasted overnight. Gastric secretion was stimulated by an intravenous infusion of tetragastrin (10 μg/kg/hr). Gastric samples were collected at 15 min intervals. After its volume was almost constant, test compound suspended in 0.1% methyl cellulose solution was injected intravenously (0.2 ml/kg). Acid concentration was determined by titrating an aliquot to pH 7.0 with 0.1N sodium hydroxide solution using automatic titration (Hiranuma RAT-11 Type). Total acid output was calculated by multiplying total volume of gastric samples by acid concentration, and percentage change of total acid output was calculated by comparing with predosing value of test compound.

(ii) Test B

Inhibition on stress ulcer

Five male Sprague-Dawley rats, aged 7 weeks and weighing about 200 g were used per group for the study on stress ulcer after the fast for 24 hours. Each animal was immobilized in a restrain cage and immersed to a level of the xiphoid in a water bath kept 22° C. The test compound suspended in 0.1% methylcellulose solution was administered orally (5 ml/kg) just before the immobilization. Seven hours later, the animals were sacrificed and their stomachs were removed. The stomach was then fixed with 2% formalin. The area of ulcers was measured for each animal. The mean area ($mm^2$) in the test animals was compared with that in the control animals.

(iii) Test C

Inhibition on ethanol ulcer

Five male Sprague-Dawley rats, aged 7 weeks and weighing about 200 g, were used per group for the study on ethanol ulcer after the fast for 24 hours.

Test compound was suspended in 0.1% methylcellulose aqueous solution, and the suspension (5 ml/kg) was orally given to each rat.

The control group was given a vehicle, i.e. 0.1% methylcellulose aqueous solution (5 ml/kg), alone in the same way.

Absolute ethanol (5 ml/kg) was orally administered 30 minutes after dosing with test compound, and one hour later, the rats were sacrificed and their stomachs were removed. The area of ulcers of each rat was measured. The mean area ($mm^2$) in the medicated group was compared with that in the control group.

Test Result

Test results are shown in the following table.

| | ANTIULCER ACTIVITY | | |
|---|---|---|---|
| | Test Method | | |
| Test Compound | Test A $ED_{50}$ (mg/Kg) | Test B $ED_{50}$ (mg/Kg) | Test C $ED_{50}$ (mg/Kg) |
| Compound of Example 3 | 0.27 | 2.7 | 6.8 |
| Gastrozepine* | 0.03 | 36.0 | 14.4 |
| Disopyramide phosphate** | — | No Effect | — |

*Known compound actually used as antiulcer medicine.
**Known compound actually used as antiarrhythmic medicine.

(II) SPASMOLYTIC ACTIVITY

Test Method

Spasmolytic activity in vivo

Mongrel dogs were anesthetized with s.c. injection of morphine chloride (10 mg/kg) and urethane (1.5 g/kg). The abdomen was incised along the midline, and a ballon filled with water was introduced into the gastric antrum or jejunum. The spontaneous contraction of the gastric antrum and jejunum were continuously recorded through the balloon connected to a pressure transducer. The test drugs were given intravenously.

The effect of the test drug is expressed as inhibitory percentage compared to the contractile magnitude obtained before the test drug. The blood pressure was also monitored with a pressure transducer through a cannula inserted in the femoral artery.

Test Result

Test results are shown in the following table.

IR (Nujol): 3350, 2300, 1590, 1460 cm$^{-1}$.

NMR (DMSO-d$_6$, δ): 1.2–1.3 (3H, m), 2.73 (3H, s), 2.90–4.16 (11H, m), 7.20–7.90 (8H, m), 8.50–8.80 (1H, m).

Analysis Calcd. for $C_{21}H_{26}N_4 2HCl$. Calcd. C 61.92, H 6.93, N 13.75. Found C 61.68, H 7.22, N 13.35.

(2) The above-mentioned crystalline product was recrystallized from diisopropyl ether to give 4-(4-meth-

| | SPASMOLYTIC ACTIVITY IN DOGS | | | | | | |
|---|---|---|---|---|---|---|---|
| | | Gastric antrum | | | Jejunum | | |
| Test Compound | Dose (μg/Kg) | Inh. (%) | Duration (min.) | Blood pressure change (%) | Inh. (%) | Duration (min.) | Blood pressure change (%) |
| Compound of Example 3 | 10 | 52 | 60 | −3 | 70 | 30 | −3 |
| | 100 | 95 | 90 | −4 | 93 | >60 | −7 |
| Timepidium Bromide* | 10 | 55 | 10 | +4 | 59 | 30 | −3 |
| 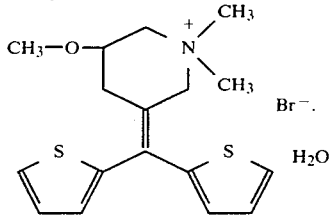 | 100 | 92 | 30 | −19 | 91 | >60 | −24 |
| Disopyramide phosphate** | 100 | 46 | 10 | +3 | 4 | 0 | +1 |
| 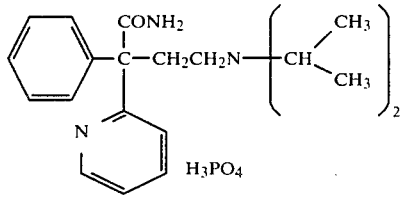 | 1000 | 88 | 60 | +5 | 85 | >60 | +14 |

*Known compound actually used as spasmolytic medicine.
**Known compound actually used as antiarrhythmic medicine.

The processes for preparation of the object compounds [I] are explained by the following examples.

EXAMPLE 1

(1) Potassium tert-butoxide (6.18 g) was added to a solution of α-phenyl-α-(2-pyridyl)acetonitrile (10.2 g) in a mixture of tert-butanol (100 ml) and xylene (5 ml) at ambient temperature under nitrogen atomosphere. After the mixture was stirred for 50 minutes, a solution of 1-(2-chloropropyl)-4-methylpiperazine (10.2 g) in tert-butanol (30 ml) was dropwise added at ambient temperature with stirring. The mixture was refluxed for 2.5 hours and the reaction mixture was evaporated under reduced pressure. The resultant residue was poured into water and extracted with ethyl acetate (50 ml×3). The extracts were combined and washed with a saturated aqueous solution of sodium chloride (50 ml), dried over magnesium sulfate and evaporated under reduced pressure to give an oily residue. The residue was subjected to column chromatography on silica gel (320 g), eluting with a mixture of chloroform and methanol (95:5) to give an oily product and a crystalline product.

The oily product dissolved in diethyl ether was treated with ethanolic hydrogen chloride to give crude crystal, which was recrystallized from ethanol to give 3-methyl4-(4-methyl-1-piperazinyl)-2-phenyl-2-(2-pyridyl)-butyonitrile dihydrochloride (6.4 g). mp 203°–205° C.

yl-1-piperazinyl)-2-phenyl-2-(2-pyridyl)-valeronitrile (1.25 g). mp 89°–90° C.

IR (Nujol): 2230, 1585, 1570, 1495 cm$^{-1}$.

NMR (CDCl$_3$, δ): 0.95 (3H, d, J=6 Hz), 2.20 (3H, s), 2.0–3.35 (11H, m), 7.0–7.70 (8H, m), 8.40–8.70 (1H, m).

Analysis Calcd. for $C_{21}H_{26}N_4$. Calcd. C 75.41, H 7.84, N 16.75. Found C 75.69, H 7.98, N 16.76.

EXAMPLE 2

The following compounds were obtained according to substantially the same manner as that of steps (1) and (2) of Example 1 from corresponding starting compounds.

(1) 2-(4-Chlorophenyl)-4-(N,N-dimethylamino)-3-methyl-2-(6-methylpyridin-2-yl)butyronitrile monohydrochloride monohydrate. mp 125°–132° C.

IR (Nujol): 3400, 2600, 2450, 1595, 1575, 1490 cm$^{-1}$.

NMR (DMSO-d$_6$, δ): 1.19–1.29 (3H, m), 2.55 (3H, s), 2.76 (3H, s), 2.80 (3H, s), 2.60–3.40 (2H, m), 3.48–3.83 (1H, m), 7.18–7.82 (7H, m), 10.86 (1H, m).

Analysis Calcd. for $C_{19}H_{22}ClN_3HCl.H_2O$. Calcd. C 59.69, H 6.59, N 10.99. Found C 60.79, H 6.33, N 11.27.

(2) 2-(4-Chlorophenyl)-4-(N,N-dimethylamino)-2-(6-methylpyridin-2-yl)valeronitrile monohydrochloride ½ hydrate. mp 92°–98° C.

IR (Nujol): 3350, 2600, 2400, 1590, 1570 cm$^{-1}$.

NMR (DMSO-d$_6$, δ): 1.12–1.3 (3H, m), 2.52 (3H, s), 2.67 (6H, broad s), 2.40–2.92 (1H, m), 3.00–3.44 (2H, m), 7.20–7.88 (7H, m), 11.44 (1H, m).

Analysis Calcd. for C$_{19}$H$_{22}$ClN$_3$HCl.½H$_2$O. Calcd. C 61.13, H 6.48, N 11.26. Found C 60.12, H 6.52, N 11.23.

(3) 2-(4-Chlorophenyl)-3-methyl-4-(4-methyl-1-piperazinyl)-2-(6-methylpyridin-2-yl)butyronitrile dihydrochloride. mp 199°–201° C.

IR (Nujol): 2420, 1590, 1570, 1490 cm$^{-1}$.

NMR (DMSO-d$_6$, δ): 1.03–1.43 (3H, s), 2.50 (3H, m), 2.78 (3H, s), 2.0–4.33 (11H, m), 7.10–7.90 (7H, m).

Analysis Calcd. for C$_{22}$H$_{27}$ClN$_4$2HCl. Calcd. C 57.97, H 6.41, N 12.29. Found C 56.66, H 6.37, N 11.84.

(4) 2-(4-Chlorophenyl)-4-(4-methyl-1-piperazinyl)-2-(6-methylpyridin-2-yl)valeronitrile dihydrochloride monohydrate. mp 165°–173° C.

IR (Nujol): 3400, 2420, 1595, 1575, 1495 cm$^{-1}$.

NMR (DMSO-d$_6$, δ): 1.03–1.40 (3H, m), 2.75 (3H, s), 2.30–3.03 (4H, m), 3.30–3.80 (10H, m), 7.18–7.90 (7H, m).

Analysis Calcd. for C$_{22}$H$_{27}$ClN$_4$2HCl.H$_2$O. Calcd. C 55.76, H 6.59, N 11.82. Found C 55.68, H 6.35, N 11.84.

EXAMPLE 3

Conc. sulfuric acid (11 ml) was added to 4-(N,N-dimethylamino)-2-phenyl-2-(2-pyridyl)-valeronitrile (6.3 g) at 0° C. and then water (1 ml) was added thereto. After being heated at 90° C. for 3 hours, the mixture was poured into ice-water, adjusted to pH 10 with 10% aqueous sodium hydroxide and extracted with ethyl acetate (50 ml×3). The extracts were combined, and washed with water, dried over magnesium sulfate and evaporated under reduced pressure. The obtained crude crystal was recrystallized from diethyl ether to give 4-(N,N-dimethylamino)-2-phenyl-2-(2-pyridyl)-valeramide (1.89 g). mp 132°–134° C.

IR (Nujol): 3200, 1675, 1635, 1585, 1490 cm$^{-1}$.

NMR (CDCl$_3$, δ): 0.72 (3H, d, J=6.5 Hz), 2.13 (6H, s), 2.0–3.46 (3H, m), 5.87 (1H, m), 6.87–7.63 (8H, m), 8.37–8.63 (1H, m), 10.63 (1H, m).

Analysis Calcd for C$_{18}$H$_{23}$N$_3$O. Calcd. C 72.69, H 7.80, N 14.13. Found C 72.47, H 7.83, N 14.17.

EXAMPLE 4

The following compounds were obtained according to substantially the same manner as that of Example 3 from corresponding starting compounds.

(1) 4-(N,N-Dimethylamino)-3-methyl-2-phenyl-2-(2-pyridyl)-butyramide dihydrochloride ½ hydrate. mp 135°–145° C.

IR (Nujol): 3370, 2700, 1675, 1610, 1530 cm$^{-1}$.

NMR (DMSO-d$_6$, δ): 1.03 (3H, d, J=6 Hz), 2.0–3.53 (8H, m), 3.53–4.13 (1H, m), 6.30–6.90 (3H, m), 6.90–8.30 (8H, m), 8.47–8.77 (1H, m), 10.37 (1H, m).

Analysis Calcd. for C$_{18}$H$_{23}$N$_3$O2HCl½H$_2$O. Calcd. C 57.00, H 6.91, N 11.08. Found C 56.87, H 7.08, N 10.37.

(2)-3-methyl4-(4-Methyl-1-piperazinyl)-2-phenyl-2-(2-pyridyl)butyramide. mp 125°–127° C.

IR (Nujol): 3280, 3150, 1675, 1585, 1570 cm$^{-1}$.

NMR (CDCl$_3$, δ): 0.98 (3H, d, J=7 Hz), 2.10 (2H, m), 2.23 (3H, s), 2.13–2.97 (8H, m), 3.31–3.63 (1H, m), 7.00–7.73 (8H, m), 8.43–8.60 (1H, m).

Analysis Calcd. for C$_{21}$H$_{28}$N$_4$O(⅓C$_6$H$_6$). Calcd C 71.56, H 8.01, N 15.90. Found C 72.50, H 8.17, N 14.99.

(3) 4-(4-methyl-1-piperazinyl)-2-phenyl-2-(2-pyridyl)-valeramide. mp 135°–136° C.

IR (Nujol): 3360, 1680, 1630, 1585 cm$^{-1}$.

NMR (CDCl$_3$, δ): 0.80 (3H, d, J=6.5 Hz), 2.27 (3H, s), 2.03–3.50 (11H, m), 5.90 (1H, m), 6.93–7.67 (8H, m), 8.43–8.60 (1H, m), 10.60 (1H, m).

Analysis Calcd. for C$_{21}$H$_{28}$N$_4$O. Calcd. C 71.56, H 8.01, N 15.90. Found C 71.79, H 8.04, N 15.68.

(4) 2-(4-Chlorophenyl)-4-(N,N-dimethylamino)-3-methyl-2-(6-methylpyridin-2-yl)butyramide.

IR (Nujol): 3440, 3350, 3140, 1675, 1645 cm$^{-1}$.

NMR (CDCl$_3$, δ): 0.98 (3H, d, J=6.5 Hz), 1.30–2.20 (2H, m), 2.22 (6H, s), 2.53 (3H, s), 2.92–3.48 (1H, m), 6.70–7.60 (7H, m).

Analysis Calcd. for C$_{19}$H$_{24}$ClN$_3$O. Calcd. C 65.98, H 6.99, N 12.15. Found C 65.56, H 6.90, N 11.70.

(5) 2-(4-Chlorophenyl)-4-(N,N-dimethylamino)-2-(6-methylpyridin-2-yl)valeramide, mp 162°–167° C.

IR (Nujol): 3220, 1660, 1590, 1575, 1490 cm$^{-1}$.

NMR (CDCl$_3$, δ): 0.75 (3H, d, J=6 Hz), 2.12 (6H, s), 1.90–2.90 (3H, m), 2.50 (3H, s), 5.90 (1H, m), 6.90–7.65 (7H, m), 10.70 (1H, m).

Analysis Calcd. for C$_{19}$H$_{24}$ClN$_3$O. Calcd. C 65.98, H 6.99, N 12.15. Found C 66.06, H 7.12, N 12.06.

(6) 2-(4-Chlorophenyl)-3-methyl-4-(4-methyl-1-piperazinyl)-2-(6-methylpyridin-2-yl)butyramide. mp 185°–189° C.

IR (Nujol): 3260, 3120, 1670, 1585, 1575 cm$^{-1}$.

NMR (CDCl$_3$, δ): 0.98 (3H, d, J=7 Hz), 1.30–2.08 (2H, m), 2.25 (3H, s), 2.08–2.90 (11H, m), 3.0–3.52 (1H, m), 6.67–7.63 (7H, m).

Analysis Calcd. for C$_{22}$H$_{29}$ClN$_4$O. Calcd. C 65.90, H 7.97, N 13.97. Found C 65.43, H 7.45, N 13.62.

(7) 2-(4-Chlorophenyl)-4-(4-methyl-1-piperazinyl)-2-(6-methylpyridin-2-yl)valeramide.

(i) Diastereoisomer A
mp 150°–152° C.

IR (Nujol): 3230, 1660, 1625, 1590, 1570 cm$^{-1}$.

NMR (CDCl$_3$, δ): 0.85 (3H, d, J=7 Hz), 2.20 (3H, s), 2.10–3.30 (11H, m), 2.53 (3H, s), 6.67–7.57 (7H, m).

Analysis Calcd. for C$_{22}$H$_{29}$ClN$_4$O. Calcd. C 65.90, H 7.29, N 13.97. Found C 66.25, H 7.36, N 13.79.

(ii) Diastereoisomer B
mp 169°–171° C.

IR (Nujol): 3270, 3140, 1678, 1585, 1575, 1490 cm$^{-1}$.

NMR (CDCl$_3$, δ): 0.82 (3H, d, J=6 Hz), 2.21 (3H, s), 1.87–3.33 (11H, m), 2.53 (3H, s), 6.0 (1H, m), 6.88–7.63 (7H, m), 10.45 (1H, m).

Analysis Calcd. for C$_{22}$H$_{29}$ClN$_4$O. Calcd. C 65.90, H 7.29, N 13.97. Found C 65.18, H 7.40, N 13.71.

What we claim is:

1. α-Aryl-α-pyridylalkanoic acid compounds of the formula:

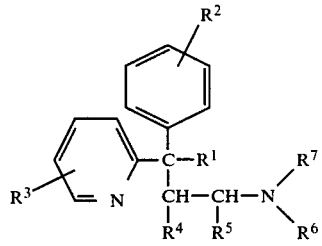

wherein
R$^1$ is carbamoyl,
R$^2$ is hydrogen or halogen,
R$^3$ is hydrogen or lower alkyl,
one of R$^4$ and R$^5$ is hydrogen and another is lower alkyl,
R$^6$ is lower alkyl, and
R$^7$ is lower alkyl,
and salts thereof.

2. The compounds of claim 1, wherein $R^2$ and $R^3$ are each hydrogen.

3. α-Aryl-α pyridylalkanoic acid compounds of the formula:

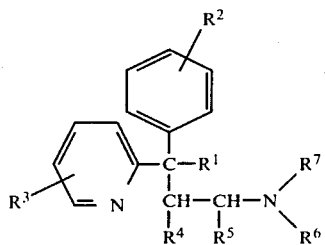

wherein
$R^1$ is carbamoyl,
$R^2$ and $R^3$ are each hydrogen,
$R^4$ is hydrogen,
$R^5$ is lower alkyl,
$R^6$ is lower alkyl,
$R^7$ is lower alkyl,
and salts thereof.

4. The compound of claim 3, which is 4-(N,N-dimethylamino)-2-phenyl-2-(2-pyridyl)valeramide.

5. An anti-ulcer, anti-spasmodic pharmaceutical composition comprising an effective amount of a compound of claim 1 in accordance with a pharmaceutically acceptable, substantially non-toxic carrier or excipient.

* * * * *